US010702141B2

(12) United States Patent
Mantysalo et al.

(10) Patent No.: US 10,702,141 B2
(45) Date of Patent: Jul. 7, 2020

(54) AUTOMATED PERIMETER (71) Applicant: Ocuspecto Oy, Turku (FI)

(72) Inventors: Tapio Mantysalo, Hevonpaa (FI); Markku Leinonen, Turku (FI)

(73) Assignee: Ocuspecto Oy, Turku (FI)

( * ) Notice: Subject to any disclaimer, the term of this patent is extended or adjusted under 35 U.S.C. 154(b) by 535 days.

(21) Appl. No.: 14/915,641

(22) PCT Filed: Sep. 2, 2014

(86) PCT No.: PCT/FI2014/050672
§ 371 (c)(1),
(2) Date: Mar. 1, 2016

(87) PCT Pub. No.: WO2015/028722
PCT Pub. Date: Mar. 5, 2015

(65) Prior Publication Data
US 2016/0249798 A1 Sep. 1, 2016

(30) Foreign Application Priority Data
Sep. 2, 2013 (FI) ...................................... 20135885

(51) Int. Cl.
*A61B 3/02* (2006.01)
*A61B 3/024* (2006.01)
(Continued)

(52) U.S. Cl.
CPC ............ *A61B 3/024* (2013.01); *A61B 3/0033* (2013.01); *A61B 3/0091* (2013.01); *A61B 3/022* (2013.01);
(Continued)

(58) Field of Classification Search
CPC ........ A61B 3/024; A61B 3/0091; A61B 3/032
(Continued)

(56) References Cited

U.S. PATENT DOCUMENTS 2,283,752 A 5/1942 Gonsett
4,559,047 A 12/1985 Kapralis et al.
(Continued)

FOREIGN PATENT DOCUMENTS

CN 1438852 A 8/2003
CN 201480060873.X 4/2018
(Continued)

OTHER PUBLICATIONS

Bodrogi et al., "Spectral Sensitivity and Additivity of Discomfort Glare Under Street and Automotive Lighting Conditions," 20 Light & Engineering 66-71 (2012).
(Continued)

*Primary Examiner* — Mahidere S Sahle
(74) *Attorney, Agent, or Firm* — James C. Lydon (57) ABSTRACT The invention relates to a perimeter or a campimeter with a visible fixation point and a method used in them. The method comprises at least the following steps:
  producing a fixation point having a first visual appearance to be shown to a patient;
  producing a stimulus shown to the patient at a stimulus time-point at a pre-defined location;
  activating a response device by the patient upon noticing the stimulus at a response time-point;
  changing the fixation point to have a second visual appearance for a fixation point second visual appearance time interval near the stimulus time-point.

11 Claims, 8 Drawing Sheets (51) Int. Cl.
  *A61B 5/16* (2006.01)
  *A61B 3/00* (2006.01)
  *A61B 3/028* (2006.01)
  *A61B 3/032* (2006.01)
  *A61B 3/06* (2006.01)
  *A61B 5/00* (2006.01)
  *A61B 3/18* (2006.01)
  *H04N 5/58* (2006.01)

(52) U.S. Cl.
  CPC .............. *A61B 3/028* (2013.01); *A61B 3/032* (2013.01); *A61B 3/063* (2013.01); *A61B 3/066* (2013.01); *A61B 3/18* (2013.01); *A61B 5/163* (2017.08); *A61B 5/7445* (2013.01); *H04N 5/58* (2013.01)

(58) Field of Classification Search
  USPC .................................................. 351/222, 224
  See application file for complete search history.

(56) References Cited

U.S. PATENT DOCUMENTS

| | | | |
|---|---|---|---|
| 4,679,920 | A | 7/1987 | Takashi et al. |
| 4,869,589 | A | 9/1989 | Blair et al. |
| 4,907,580 | A | 3/1990 | Leonardi |
| D309,465 | S | 7/1990 | Russell |
| 5,035,500 | A | 7/1991 | Rorabaugh et al. |
| 5,183,059 | A | 2/1993 | Leonardi |
| 5,422,690 | A | 6/1995 | Rothberg et al. |
| 5,459,536 | A | 10/1995 | Shalon et al. |
| 5,565,949 | A | 10/1996 | Kasha, Jr. |
| 5,592,247 | A | 1/1997 | Trokel |
| 5,740,550 | A | 4/1998 | Yavitz |
| 5,769,806 | A | 6/1998 | Radow |
| 5,825,460 | A | 10/1998 | Kohayakawa |
| 5,920,375 | A | 7/1999 | Fahle et al. |
| D421,124 | S | 2/2000 | Yavitz |
| D424,691 | S | 5/2000 | Yavitz |
| D425,623 | S | 5/2000 | Funk |
| D436,665 | S | 1/2001 | Becker |
| D440,660 | S | 4/2001 | Sternberg |
| D442,693 | S | 5/2001 | Sternberg et al. |
| D444,236 | S | 6/2001 | Koop et al. |
| 6,612,700 | B2 | 9/2003 | Walther |
| 6,817,715 | B2 | 11/2004 | Leinonen |
| D533,572 | S | 12/2006 | Howard et al. |
| 7,265,917 | B2 | 9/2007 | Kugler et al. |
| D552,736 | S | 10/2007 | Yamaoka |
| 7,478,911 | B2 | 1/2009 | Inakagata et al. |
| D607,562 | S | 1/2010 | Heine et al. |
| D614,774 | S | 4/2010 | Gausmann et al. |
| D639,441 | S | 6/2011 | Sferle |
| 8,038,297 | B1 | 10/2011 | Hofeldt |
| D674,903 | S | 1/2013 | Harder |
| D698,444 | S | 1/2014 | Mensink |
| 8,691,193 | B2 | 4/2014 | Rodriguez et al. |
| D705,430 | S | 5/2014 | Sekine |
| D709,199 | S | 7/2014 | Kambe et al. |
| D723,698 | S | 3/2015 | Cockley |
| D734,471 | S | 7/2015 | Pollanen |
| 2004/0105073 | A1 | 6/2004 | Maddalena et al. |
| 2005/0068498 | A1 | 3/2005 | Suzuki |
| 2005/0128434 | A1 | 6/2005 | Ianchulev et al. |
| 2006/0001831 | A1 | 1/2006 | Sumiya |
| 2006/0087618 | A1 | 4/2006 | Smart et al. |
| 2006/0114414 | A1 | 6/2006 | McGrath et al. |
| 2007/0182928 | A1 | 8/2007 | Sabel |
| 2008/0212032 | A1 | 9/2008 | Seiller et al. |
| 2009/0051877 | A1 | 2/2009 | Delahunt et al. |
| 2009/0303626 | A1 | 12/2009 | Xalter et al. |
| 2010/0128222 | A1 | 5/2010 | Donaldson |
| 2010/0171926 | A1 | 7/2010 | Padula |
| 2010/0208254 | A1 | 8/2010 | Arnz |
| 2012/0081669 | A1 | 4/2012 | Feiertag et al. |
| 2012/0092620 | A1 | 4/2012 | Epitropoulos |
| 2014/0340642 | A1 | 11/2014 | You et al. |
| 2014/0362346 | A1 | 12/2014 | Leinonen et al. |

FOREIGN PATENT DOCUMENTS

| | | |
|---|---|---|
| EP | 2561799 | 2/2013 |
| GB | 2397391 | 7/2004 |
| JP | H024309 A | 1/1990 |
| JP | 07299033 A | 11/1995 |
| JP | 0880281 A | 3/1996 |
| JP | H0866360 A | 3/1996 |
| JP | 2000310983 A | 11/2000 |
| JP | 2002209849 A | 7/2002 |
| JP | 2003088501 A | 3/2003 |
| JP | 200393344 | 4/2003 |
| JP | 2004317530 A | 11/2004 |
| JP | 2005256860 A | 9/2005 |
| JP | 2005296402 A | 10/2005 |
| JP | 200614766 | 1/2006 |
| JP | 2006267225 A | 10/2006 |
| JP | 2006304811 A | 11/2006 |
| JP | 2007277239 A | 10/2007 |
| JP | 2011139914 A | 7/2011 |
| JP | 2016539603 | 5/2018 |
| WO | 02/00105 A1 | 1/2002 |
| WO | 2005093679 | 10/2005 |
| WO | 2008005848 | 1/2008 |
| WO | 2008078106 | 7/2008 |
| WO | 2013094995 | 6/2013 |
| WO | 2013096473 A1 | 6/2013 |
| WO | 2013120075 A1 | 8/2013 |
| WO | 2015023676 | 2/2015 |

OTHER PUBLICATIONS

Charoensap et al., "Evaluation of Discomfort Glare From Color LEDs Under Different Illuminance," Proceedings of the 1st Asia Color Association Conference (ACA2013) Paper OA31 Thanyaburi: Blooming Color for Life 62 (Dec. 11-14, 2013).

Fekete et al., "Spectral Discomfort Glare Sensitivity Investigations," 30 Ophthal. Physiol. Opt. 182 (2010).

Kotani et al., "Visual Field Screening System by Using Overlapped Fixation Patterns," 95 Electronics and Communications in Japan 29 (2012).

Namiki et al., "Measurement of Glare Disability Using an Automated Perimeter," 18 J. Cataract Refract. Surg. 391 (1992).

Niedling et al., "Influence of a Glare Sources Spectrum on Discomfort and Disability Glare Under Mesopic Conditions," Proceedings of CIE Centenary Conference Towards a New Century of Light 340 (2013).

Ryckaert et al., "Linear LED Tubes versus Fluorescent Lamps: An Evaluation," 49 Energy and Buildings 429 (2012).

Sivak et al., "Blue Content of LED Headlamps and Discomfort Glare," Report No. UMTRI-2005-2 (Univ. Mich. 2005).

Zhang et al., "Effect of the Correlated Color Temperature of Light on Overhead Glare in Offices," 44 Proceedings of the SID Symposium Digest of Technical Papers 1096 (2013).

Zydek et al., "A New Concept of Disability Glare Under Traffic Lighting Conditions: Experimental Setup, Results and Analysis of Spectral Sensitivity," 14 Proceedings of the 9th International Symposium on Automotive Lighting 362 (2011).

Partial Translation of Official Action in Japanese application 2016-539602.

AUTOMATED PERIMETER

TECHNICAL FIELD OF THE INVENTION

The invention relates to an automated perimeter or campimeter, such as a standard automated perimeter, and a new method used in it.

TECHNICAL BACKGROUND

In present standard automated perimetry (SAP), as well as most of other perimeters, a patient looks at a fixation point. The patient indicates orally or presses a button when he/she sees a stimulus, i.e. light flash on a canvas or other surface. From the patients response it is determined if the patient saw the stimulus or not. By varying the stimulus location and intensity a map of visual field for the patient is built.

There are certain problems in the present standard automatic perimetry. The patient easily loses interest to staring at fixation point, so the fixation is not steady. An eye might involuntary follow the stimulus, rather than fixation point—this phenomenon is increased if the patient has vision or neural problems. Staring at one point is not normal, and causes fatigue, which causes loss of fixation and attention and therefore incorrect visual field test results.

WO 2008/078106 A2 and WO 2013/094995 A1 present some solutions for enhancing the fixation of a tested person.

OBJECT OF THE INVENTION

It is an object of the present invention to reduce the above-mentioned problems appearing in prior art.

The present invention has especially an object of providing for a comfortable and easy-to-use method and device for standard automated perimetry.

An object of the present invention is to provide more reliable results from standard automated perimetry.

An object of the present invention is to improve visual field measurements, used for example to screen and follow diseases which may cause visual field loss, such as glaucoma, retinal diseases or in some cases head injury or stroke.

SUMMARY OF THE INVENTION

Among others, in order to realize the objects mentioned above, devices and methods and other objects according to the invention are characterized by what is presented in the characterizing parts of the enclosed independent claims.

The embodiments, examples and advantages mentioned in this text relate, where applicable, as well to any devices, methods as to uses according to the invention, even though it is not always specifically mentioned.

A typical method in a perimeter or a campimeter with a visible fixation point comprises at least the following steps:
producing a fixation point having a first visual appearance to be shown to a patient;
producing a stimulus shown to the patient at a stimulus time-point at a pre-defined location in the perimeter or campimeter, typically in the visual field of the patient;
activating a response device by the patient upon noticing the stimulus at a response time-point;
changing the fixation point to have a second visual appearance for a fixation point second visual appearance time interval near the stimulus time-point.

A typical automated perimeter according to the invention comprises means for producing a fixation point having a first visual appearance to be shown to a patient;
means for producing a stimulus shown to the patient at a stimulus time-point and at a pre-defined visual field location;
a response device, such as a push button, adapted to be activated by the patient upon noticing the stimulus at a response time-point;
where the means for producing a fixation point are arranged to change the fixation point to have a second visual appearance for a fixation point second visual appearance time interval near the stimulus time-point.

The visual stimulus typically has a defined intensity, color and duration. The visual stimulus is e.g. a small flash of light. The duration of the visual stimulus may be e.g. 10-300 ms or 100 ms.

The first and second visual appearances of the fixation point can be chosen to be suitable to any specific situation. In one embodiment the first visual appearance is a symbol comprising a ring, such as letter "O". In one embodiment the second visual appearance is a symbol comprising crossed lines, such as "+" i.e. the plus-sign or letter "X".

The first and second fixation points can take any usable shape or color or intensity. In some embodiments also the origo of the visual field is measured: then, the first and especially the second visual appearance of the fixation point must be hollow to give place to the stimulus which then appears at the same visual field location as the fixation point (origo of the visual field is at the fixation point when the patient is staring at the fixation point). First or second visual appearance could also be resembling the stimulus in appearance, in which case the instruction to the patient could be to detect if the "stimulus" jumps somewhere or not.

The response device may be e.g. one or more buttons. Thus the activating a response device may mean e.g. that the patient pushes a relevant button. The patient may also respond e.g. orally, or another means, such as pointing where the stimulus appeared (could be e.g. touch screen). Also for example a joystick or handle (to be pulled or pushed) could be used as the response device.

Normally, if no activation of the response device by the patient is noticed, it is interpreted that the stimulus was not seen.

It has now been found out that if the fixation point is of different visual appearance at or close to the time-point when a stimulus is shown, the patient will find the fixation point interesting. This provides meaningful information to his/her task: it tells when a stimulus should appear in the perimeter surface. This ensures or at least increases the possibility that the patient looks at the fixation object with foveal vision at all times. In other words: because the fixation point is more interesting, it also reduces fatigue, and the impact is better eye fixation and better attention, and therefore more accurate and repeatable results. The fixation point should be so small and dim it is barely visible: only then the first and second visual appearances are only visible with foveal (the most accurate) vision.

It often happens that the patient's eye or eyes involuntarily start to follow the stimulus, although the task is to look at the fixation point. In case the patient has neuro-visual problems, the patient will find it easier to return his/her eye/eyes back to the fixation point when the fixation point is visually interesting and meaningful, i.e. it tells when the next stimulus will appear (or has just appeared). The easier return of the eye to the fixation point also reduces fatigue.

Testing visual field with the invention is faster than normal in case of visual field problems, such as glaucoma.

Even patients with neuro-visual problems can most often do a threshold test in one go. In today's automated perimetry it is normal that a test has to be interrupted several times, for minutes, for letting the patient rest. So the invention also reduces time needed for automated visual field testing.

The fixation point and stimulus are produced on any suitable surface, such as a perimeter surface or a suitable electrical display device or projector. Perimeters, displays, projectors and suitable means to use them such as computers and computer programs are well known means for producing a fixation point and a stimulus. Time-points, visual field locations, time intervals and responses by the user are processed, recorded, maintained and calculated e.g. in a computer with a memory. The computer may be a part of the perimeter device used with the invention or it may be connected to it and a response device e.g. via any suitable electric and data transfer connections.

In an embodiment, in order the fixation point to be of low enough intensity to force the patient to constantly look at it with fovea, in the beginning of the test sequence the contrast sensitivity of the eye can be measured with stimuli close to the fixation point. This value can be used to calculate the intensity and size of the fixation point.

In an embodiment the means for producing a fixation point change the fixation point back to have the first visual appearance after the fixation point second visual appearance time interval has ended or after the patient has responded. This way the patient knows that at least for the moment a new stimulus will not be presented.

In some embodiments the fixation point second visual appearance time interval is not started earlier than 1 second or 200 ms or less than 100 ms before stimulus time-point. In an embodiment the fixation point second visual appearance time interval is started at the stimulus time-point. In some embodiments the fixation point second visual appearance time interval is started after the stimulus time-point, e.g. 0-500 ms, 0-1000 ms, 0-2000 ms or 500-1000 ms after the stimulus time-point. These time intervals may be needed in order to reduce the probability that the patient's eye starts moving away from the fixation point in order to seek a stimulus.

In one embodiment the fixation point second visual appearance time interval is not ended earlier than 100 ms, 500 ms. 1 second, 2 seconds or 3 seconds after the stimulus time-point, or after the fixation point second visual appearance is shown, or after patient has responded. This is done in order to give the patient time to recognize the changed fixation point visual appearance, but also to give the patient a bit of sense of urgency to respond to seen stimulus, so that delayed response will not affect correctness of test and/or increase total test time when testing multiple steps. In some embodiments the start and end of the fixation point second visual appearance time interval may be altered before or during the test in order to make it suitable for needs of the patient or the test.

In one embodiment the response of the patient and knowledge of whether the patient activates the response device during a response time interval or not is recorded. The response time interval may be the same or have the same duration as the fixation point second visual appearance time interval. Typically, only responses given during response time interval may be considered as valid responses.

In one embodiment the fixation point is changed to a third visual appearance, a "do-not-response-even-if-you-see-a-stimulus"-appearance for a time interval near the stimulus time-point. When the third visual appearance is shown the patient should not respond even if he/she saw the stimulus. This can be used to check that the patient is really looking at the fixation point.

As is known from the prior art, test normally includes recording responses to a number of stimuli, produced for the patient one after another. In one embodiment a second stimulus is shown to the patient at a second stimulus time-point after a time interval between the stimuli. The time interval between the stimuli can be measured from either the previous stimulus time-point or the previous response time-point. Time interval between the stimuli may be e.g. 1 s to 4 s and depend on patient reaction time, which can be calculated for example presenting some very bright stimuli which the patient is known to see at very high probability. Time interval should be longer than a typical reaction time of the patient, but not too long (e.g. less than two or three times the typical reaction time), so that the complete test procedure does not take too long.

In an embodiment a new stimulus of pre-defined intensity and duration is shown in a pre-defined location of visual field, assuming the eye is still looking at the fixation point.

In one embodiment the stimulus time interval is varied. The variation may be done in pre-defined sequences or randomized. This will make the armed fixation point even more interesting, as the time of appearance of stimulus cannot be predicted and the user really has to look at the fixation point in order to respond at the correct time when he/she sees the stimulus.

In one embodiment the position of the fixation point shown to a patient is varied during the test. The fixation object may e.g. move slowly or with small steps on the perimeter surface, in order to help the patient to keep fixation to the fixation object, and to allow testing more test points with a relatively small perimeter surface.

In one embodiment the invention is used with a stand-alone medical device for testing a patient, which comprises in one-piece configuration:
  a first testing device comprising a perimeter surface having a first side to be viewed by the patient during testing and second side not to be seen by the patient during testing,
  one or more second testing devices from the group of:
  a) a visual acuity measurement device to be viewed by the patient during testing of visual acuity,
  b) a contrast sensitivity testing device to be viewed by the patient during testing of contrast sensitivity,
  c) a glare testing device to be viewed by the patient during testing of glare,
  user interface device for controlling the use of the first and second testing devices.

This stand-alone medical device may be used in a method for testing a patient with a stand-alone medical device in one-piece configuration described later in this text. This stand-alone medical device may also be used without the present SAP invention and/or in combination with some other embodiment or feature mentioned in this text. This stand-alone medical device can measure some or most, if not all of the following functional abilities of a person being tested: functioning of the visual system, vision, attention, perceptual skills, memory, decision making, and reaction time. This stand-alone medical device can assess various aspects of function of the visual system, such as visual field, visual search ability, visual decision making, saccadic eye movement, visual acuity, contrast sensitivity, sensitivity to glare and spatial short term memory. It may provide for a reliable and easy-to-use method and device to test whether a person fulfils driver requirements for safe driving.

This invention, using the second visual appearance of the fixation point, can be used in various types of perimeters with a fixation point, e.g. high-pass resolution perimetry, short wavelength sensitive perimetry, flicker perimetry, pupil perimetry, Aulhorn's Snow field campimetry, motion perimetry, frequency doubling technology perimetry, rarebit perimetry, multifocal VEP and in some embodiments of multi-fixation perimetry, in addition to standard automated perimetry (SAP). Theory, use and function of perimeters is known in the art and not explained in full detail in this text.

One aspect of the invention is a computer program product encoding a computer program of instructions for executing a computer process according to the method of the invention. Embodiments of the method use such a computer program and embodiments of the apparatus comprise such a computer program.

One aspect of the invention is a computer program distribution medium readable by a computer and encoding a computer program of instructions for executing a computer process according to the method of the invention.

DESCRIPTION OF SOME POSSIBLE EMBODIMENTS

In this text the examples mainly speak of assessing whether a person fulfils driver requirements for safe driving, but the medical device and method according to the invention may be used in a variety of situations, e.g. diagnosing disease, job selection, visual competence assessment, school or community screenings, military selection, and disability classifications.

One method for testing a patient with a stand-alone medical device in one-piece configuration comprises at least the following steps:
testing visual field of the patient with a first testing device comprising a perimeter device;
testing one or more second tests with a second testing device, the second tests selected from the group of:
a) testing of visual acuity,
b) testing of contrast sensitivity,
c) testing of glare;
controlling the use of the first and second testing devices with a user interface device.

The medical device being stand-alone means that in a normal use situation it is capable of functioning alone, save perhaps electric power connections. In an embodiment the device comprises rechargeable batteries, thereby also removing the need for electric power connections during normal use.

The medical device being of one-piece configuration means that in a normal use situation necessary parts needed for testing a patient are comprised in one single entity. Some parts are may be turnable, e.g. hinged together and it is naturally possible that some parts may be disconnectable from each other. In an embodiment the medical device is of one-piece configuration in normal use, but also when transported or stored without actually using it.

A typical first testing device comprises a perimeter surface, i.e. a perimeter device which is a medical diagnostic device for human visual field testing. The perimeter surface has a first side to be viewed by the patient during testing and second side not to be seen by the patient during testing. Also other tests, e.g. neuropsychological tests can be run on the perimeter surface. In an embodiment the first side of the perimeter surface has a curved shape, the concave surface arranged towards the first side of the perimeter surface, i.e. towards the patient being tested.

The perimeter should be large enough to be capable of measuring visual field size. Perimeters and their use is well known in the art and therefore not explained in detail here. The perimeter can be e.g. a standard automated perimeter or a multi-fixation perimeter.

Now it has now been found that unexpected advantages may be achieved if one or more second testing device is integrated in the same stand-alone device with the perimeter. In An embodiment the second testing device is selected from the group of:
a visual acuity measurement device,
a contrast sensitivity testing device,
a glare testing device.

The second testing device is arranged to be viewed by the patient, i.e. it is visible to the first side of the perimeter surface during the test it performs. The second testing devices and second tests can include other tests too, e.g. neuropsychological tests. Glare testing means any type of glare tests. In an embodiment of the invention the glare testing comprises testing of one or more of the following types of glare: disability glare, discomfort glare, adaptation glare. Glare testing device is arranged capable of testing one or more of said types of glare. The above mentioned second testing devices and second tests, i.e. visual acuity measurement, a contrast sensitivity testing and a glare testing, are as such known to the art, therefore they are not explained in further detail here.

Further, a medical device may comprise a user interface device for controlling the use of the first and second testing devices. In an embodiment the user interface device is at least for a limited time useable and visible for the supervising person only, that is, to the second side of the perimeter surface. When the device is a stand-alone, one-piece device, all tests can easily be controlled with one single user interface device.

It is possible that the tests on the first and second testing devices are performed without a computer in the medical device itself. But in an embodiment of the invention the medical device comprises a computer with memory and a computer program code to be run on the computer memory. The computer program would then be arranged to perform the tests on the first and/or second testing devices. The computers and computer programs and data connections needed are known in the art. Computer programs can be made to perform effective testing.

In an embodiment of the invention the medical device comprises a display unit for the one or more second testing devices. The display unit would comprise a display to be viewed by the patient during testing. The display unit is arranged to show elements of the second visual test to be tested on the display. The display unit thus works as stimulus and test symbol (i.e. optotype) presentation device for e.g. visual acuity, contrast sensitivity, glare tests. In an embodiment the computer program would control what is shown on the display. Electrical displays are very effective in showing elements in the tests mentioned above. The display of the display unit may be e.g. an LCD panel.

In an embodiment of the invention the user interface device comprises the display unit, which is also used as the second testing device.

In an embodiment of the invention the computer is situated in the device of the invention, e.g. in the display unit or inside the perimeter surface.

In an embodiment of the invention the user interface device for controlling the use of the first and second testing devices is in the display unit. The display unit may comprise mechanical buttons, switches or similar, but it is possible to arrange these control means into a touchscreen, which is an electronic visual display that the user can control through simple or multi-touch gestures by touching the screen with one or more fingers. The display of the display unit may be this touchscreen for controlling the use of the first and second testing devices. In an embodiment of the invention the same display functions as a touchscreen for controlling the use of the first and second testing devices and as a display showing elements of the second visual test to be tested for the patient. The display unit may be a tablet computer or another portable device such as a phone.

In an embodiment of the invention the display unit is arranged turnable between at least two positions, i.e. in the first and second position. In the first position the display can be viewed from the first side of the perimeter surface, i.e. by the patient to be tested. In the second position the display can be viewed from the second side of the perimeter surface, i.e. by the person supervising the test. The display unit may be kept in the second position e.g. when performing a test with the first testing device, i.e. with the perimeter surface. This way the person supervising the test may supervise and control the test with the display unit. When turned into the first position, the display can function as a display showing elements of the second visual test to be tested for the patient.

If the display unit is a portable device such as a tablet computer or a phone, the medical device may comprise one or more attaching points such as a holder or a bracket or a support where the display unit may be releasebly attached. E.g. one attaching point may be arranged on the first side of the perimeter surface or in such way that the display may be seen and used from the first side. Also one attaching point may be arranged on the second side of the perimeter surface or in such way that the display may be seen and used from the second side. An attaching point for the portable device may be such that the portable device can be attached to it in at least two positions: the display towards the first side or towards the second side.

An integrated and turnable display unit provides simplicity and cost-efficiency. The efficiency of the second tests is enhanced when the display is turned to the first side of the perimeter surface. That is because the display is then surrounded by the large perimeter surface, whereby the visual field of the person to be tested is kept free of disturbing visual objects which would interfere with the test stimuli presented on the display panel and disturb the concentration of the person.

In an embodiment of the invention the perimeter surface is arranged foldable between at least two positions, i.e. a use position and a transport position. In the use position the perimeter surface is arranged open and the first side of the perimeter surface may be viewed by the patient. In transport position the perimeter surface is folded so that at least a part of the first side of the perimeter surface is not viewable by the patient and more protected. Also, in transport position the perimeter surface takes less space and and makes the device easier to transport or store between uses. If the display unit is a portable device, its transport position may be such, that when attached to its attaching point, the display is turned against the first or second side of the perimeter surface.

In an embodiment of the invention the display unit is arranged turnable into a transport position, where the display is arranged against the first side of the perimeter surface and not viewable by the patient. This protects the display and makes the device easier to transport or store between uses.

In further embodiments of the invention the medical device has a handle e.g. on the top of the perimeter surface for easy portability. In an embodiment a support leg, for allowing the device to be kept in a suitable position e.g. on a table, is arranged turnable on the device. The turnable support leg may assist in arranging the perimeter surface and/or display unit to be in a suitable position, e.g. perpendicular to the patient The support leg may also be arranged to be used as a carrying handle and for hanging the device e.g. on a wall.

In an embodiment of the invention the medical device comprises ambient light sensors arranged to detect lighting conditions around the device and arranged to monitor and/or adjust the performance of the first and/or second testing devices and the second tests. Ambient light sensors are well known as such. They are used to detect light or brightness in a similar way as the human eye. They are used wherever the settings of a system have to be adjusted to the ambient light conditions as perceived by humans. Ambient light sensors may be integrated in the perimeter, in the display unit or elsewhere in the device.

In an embodiment of the invention ambient light sensors are used to monitor the lighting behind the device in order to detect too bright areas, e.g. window, or too dark areas in the examination room which would disturb the visibility of the test stimuli which are presented by the device for the person.

In an embodiment of the invention ambient light sensors are used to monitor the ambient lighting of the room which illuminates the first surface of the perimeter surface in order to detect if the illumination in different parts of the surface of the device is uniform and adequate.

In an embodiment of the invention ambient light sensors are used to adjust the intensity i.e. luminance of the perimeter stimuli and fixation objects during the test based on the illumination of the perimeter surface so that the luminance contrast can be set at the desired level. Luminance contrast $C_W=(L_s-L_b)/L_b$; where $L_s$ is luminance of the stimulus and $L_b$ is the luminance of the background, i.e. the perimeter surface.

In an embodiment of the invention ambient light sensors are used to adjust the brightness i.e. luminance and contrast of the display of the display unit during the test according to the illumination of the perimeter surface.

In an embodiment of the invention ambient light sensors are used to adjust the glare light intensity according to the illumination of the perimeter surface.

In an embodiment of the invention the medical device comprises proximity sensors arranged to detect the position of the patient and arranged to monitor and/or adjust the performance of the first and/or second testing devices. Proximity sensors may be integrated in the perimeter, in the display unit or elsewhere in the device.

In some embodiments of the invention the optotype size showed to the patient on the display unit when performing visual acuity measurement, contrast sensitivity testing or glare testing is automatically varied depending on the distance of the patient measured by the proximity sensors. Normally, the further from the device the patient is, the larger the optotype size showed to the patient.

In some embodiments of the invention the ambient light and proximity sensors are used for validating the measurement conditions during testing. If e.g. the patient moves into an invalid position the device may give a warning or guidance to the patient or the test operator/supervisor to correct the patient's position.

In some embodiments of the invention the perimeter measurement grid, i.e. visual field test points produced e.g.

by light matrixes on the perimeter surface, are automatically adjusted according to the patient head position i.e. distance from the perimeter surface.

In an embodiment of the invention the medical device comprises one or more glare lights or glare sensitivity test lights to be lighted towards the patient during testing of glare sensitivity or other glare tests. The glare lights may be integrated in the perimeter, in the display unit or elsewhere in the device. In an embodiment of the invention the glare light spectrum is arranged to be varied, e.g. to test sensitivity differences to different light sources, such as halogen or xenon headlamps. The glare light spectrum can be varied e.g. by producing the glare light with lamps e.g. LEDs of different colors and by varying their effect.

In an embodiment of the invention the first testing device comprises at least one light matrix, such as a LED (light-emitting diode) matrix or an OLED (organic light-emitting diode) matrix or an LCD (liquid-crystal display) matrix. The light matrix or matrixes are arranged capable of displaying perimeter stimulus and/or fixation objects to the first side of the perimeter surface, i.e. to be seen by the patient. Perimeter stimulus and/or fixation objects are figures or shapes that can be discriminated from each other by the patient during testing. Lights on the perimeter surface are known as such, but light matrixes enable new kind of effective tests, as the light matrixes (such as implemented with LEDS) can provide more light output and therefore the dynamic range will be higher than with commercially available large display panels. Curved shape of the perimeter surface built with separate display matrix units offers the possibility extend visual field measurements to over 90 degrees from fixation point, which is not possible with perimeter using only one or two flat display panels.

In an embodiment of the invention the first side of the perimeter surface is covered with a translucent layer, made e.g. of suitable plastic material. The layer is arranged to hide the light matrix from the patient when the light matrix is not lighted. But when a light in the light matrix is lighted, the layer is arranged to let light through it in order to show the position of the perimeter stimulus and/or fixation objects to the patient. When the perimeter translucent surface is matt, not glossy, there will be an advantage over LCD or OLED displays that the perimeter testing can be executed under normal room lighting without fear of reflections on display disturbing the measurement results.

In an embodiment of the invention the perimeter surface has light sources, such as light openings or additional LEDs or other light sources towards its second side. These lights or openings are situated at the positions where the lights, e.g. LEDs of the light matrix are situated on the first side of the perimeter surface. This way a doctor or other person supervising the test from the second side of the perimeter surface can simultaneously see both where the patient is looking, and also the position of the lighted light, i.e. a fixation object or visual stimulus.

In an embodiment of the invention the medical device, e.g. the perimeter surface, incorporates two or more loudspeakers. Loudspeakers may be used e.g. for testing sensory integration of vision and visual oculomotor function where auditory system can be assessed using localizing sound stimuli from the loudspeakers of the device which guide the gaze to find the tiny fixation objects on the perimeter surface. Loudspeakers may also be used when assessing spatial hearing and sensory integration (i.e. spatial hearing & spatial vision). Loudspeakers allow auditory guidance of the saccades of the test subject in perimeter to locate a fixation object which is detectable only by foveal vision. The loudspeakers may be situated e.g. on the first surface of the perimeter surface, hidden behind the translucent layer.

In an embodiment of the invention the medical device comprises at least one attachment point for a camera or eye-tracker for recording the eye movements of the patient during testing. The attachment point may be situated e.g. on an edge of the perimeter surface.

The display of the display unit can be used for many kinds of neuropsychological tests, e.g. memory guided saccade, anti-saccade or the Trailmaker test. The perimeter surface can also be used for memory guided saccade and anti-saccade testing.

A multi-fixation perimeter can also be implemented as a First Pulse Perimeter (FPP) so that there will be multiple supra-threshold stimuli flashed to the patient, of which one will be shown earlier, e.g. 20 ms to 500 ms earlier, and the visual search task is to recognize which stimulus was presented earlier (the correct visual cue will be found under this). This kind of perimeter will measure the magno-cellular routes of the visual system, potentially useful for, e.g. glaucoma.

Another embodiment and a possible use of the device is so called critical symbol size testing which can be used e.g. when testing of visual acuity, contrast sensitivity or sensitivity to glare of a person. In prior art of this kind of testing a person has to identify a symbol of variable size or contrast visible on the display unit with or without glare light. In the present invention also the reaction time starting from the appearance of the symbol to be identified on the display panel to the pressing of the correct button on the device or the remote controller indicating correct identification of the symbol is recorded. The smallest symbol size which doesn't cause prolongation of the reaction time, when continually reducing the size of symbols to be identified, is named as 'critical symbol size'. This critical symbol size is an important indication of an individual's performance in relation to certain daily activities such as driving, reading, and video display terminal works. When the person is using extended time (i.e. reaction time for identification of the symbol is longer than at critical symbol size) he/she can identify even smaller symbols than the critical symbol size, the smallest symbol size which can be identified using extended time being the 'threshold size' which is used for calculating visual acuity or contrast sensitivity. The difference in symbol sizes for critical symbol size and threshold size varies for various conditions of visual system. The enlargement of the critical symbol size can be an indication of ocular disease (e.g. ocular surface disease i.e. dry eye, mild cataract or posterior capsule opacification after cataract surgery, epiretinal membranes of macular area of fundus of the eye) even if the threshold value of the visual acuity or contrast sensitivity is in the normal range.

One of the advantages of some embodiments is how ambulatory use, i.e. portability of the device is made possible, e.g.: the device is of one-piece configuration; parts of the device e.g. perimeter panel, display unit, support leg, can be made foldable to reduce space needed and to protect the device; the device can be battery operated; the device is easily made light-weight (e.g. less than 5 kg); the support leg may form a handle for hanging on the wall for storage or for easy carrying of the device.

One advantage of some embodiments is that the automatic monitoring of the testing environment makes it possible to control for all important factors which have an effect on the measurement results made with the device, e.g.: the accuracy of the results are better than before; automatic operation of the testing procedure becomes possible; the device can notify the test supervisor or operator if the test situation is outside the limits of reliable operation and suggest actions to correct them; the test supervisor or operator doesn't have to be an expert in vision testing because the device takes care of possible sources of errors caused by inconsistent environment.

One advantage of some embodiments is that combining different tests and devices together gives unexpected synergy, e.g. the same proximity sensors and ambient light sensors can be used with tests with the perimeters surface and with the second testing devices, e.g. on the display unit. In other words, because the display unit can be turned to the first side of the perimeter surface the proximity sensors and ambient light meters for perimeter tests can be used in the tests for the visual acuity, contrast sensitivity and glare.

One advantage of some embodiments is that the testing of visual acuity, testing of contrast sensitivity and testing of glare, can be made automatic. In other words, the test subject replies to visual questions (i.e. optotypes) using a remote controller or pressing buttons or touch screen on the device itself. Many existing products only show visual questions but the test operator/supervisor must manually record the answers of the patient, decide whether the answer is right or wrong, step to next optotype in the algorithm and finally write down the results.

The applicants own patent application PCT/FI2013/050266 can be seen for more examples and details on the tests mentioned in this text. The application PCT/FI2013/050266, especially its text and especially the examples are hereby incorporated herein by reference.

BRIEF DESCRIPTION OF THE FIGURES

The invention is described in more detail below with reference to the enclosed schematic drawing, in which.

DETAILED DESCRIPTION OF THE EXAMPLES OF THE FIGURES

For the sake of clarity, the same reference numbers are used for corresponding parts in different embodiments.

FIGS. 1 to 6 show a stand-alone medical device 1 for testing a patient according to the invention. The device 1 comprises a first testing device, i.e. a perimeter surface 2. The perimeter surface has a first side 3 to be viewed by the patient during testing and second side 4 not to be seen by the patient during testing. A display unit 5 is arranged turnable with hinge 6 below the perimeter surface. The display unit comprises a touchscreen display 7, which functions both as a user interface device and as a display to be viewed by the patient during testing of so called second tests. A computer controlling the use of the medical device is integrated inside the display unit 5 or the perimeter surface 2. The second tests, which are at least partly shown on the display 7, may comprise e.g. visual acuity measurement, contrast sensitivity testing or glare testing.

Figure 1:
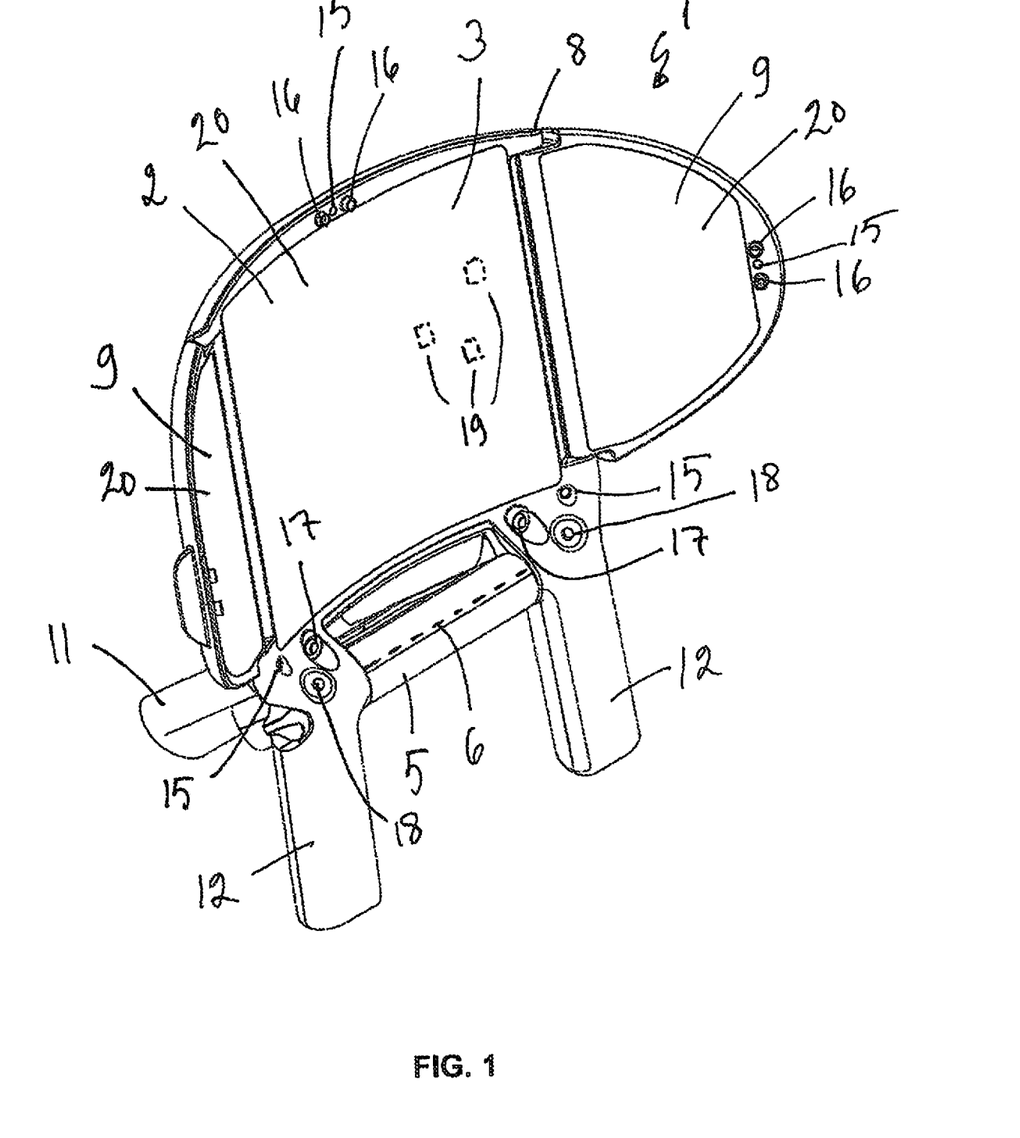
FIG. 1 shows a medical device according to the invention from the first side of the perimeter surface in a first situation.
Figure 2:
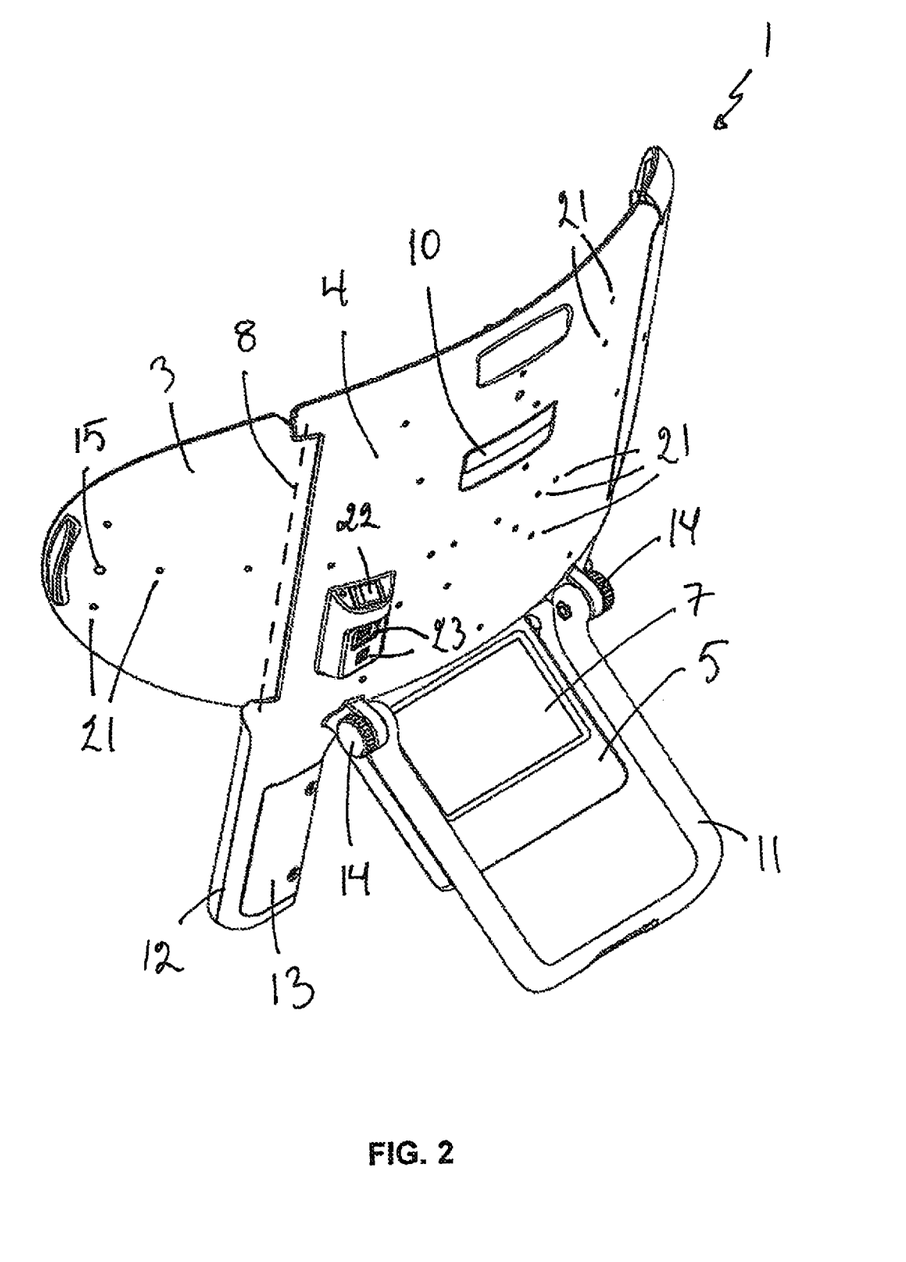
FIG. 2 shows the medical device of FIG. 1 from the second side of the perimeter surface.
Figure 3:
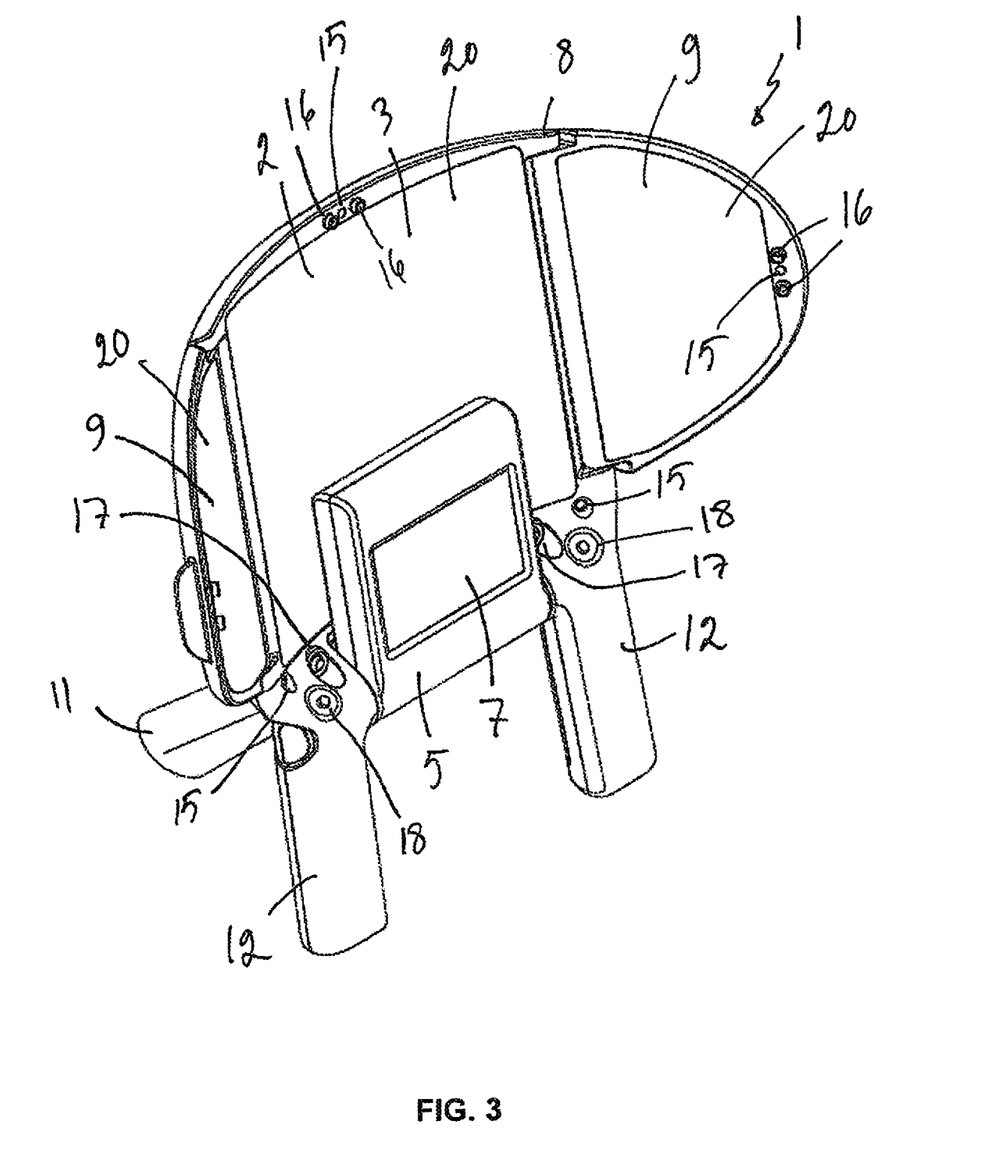
FIG. 3 shows a medical device according to the invention from the first side of the perimeter surface in a first second situation.
Figure 4:
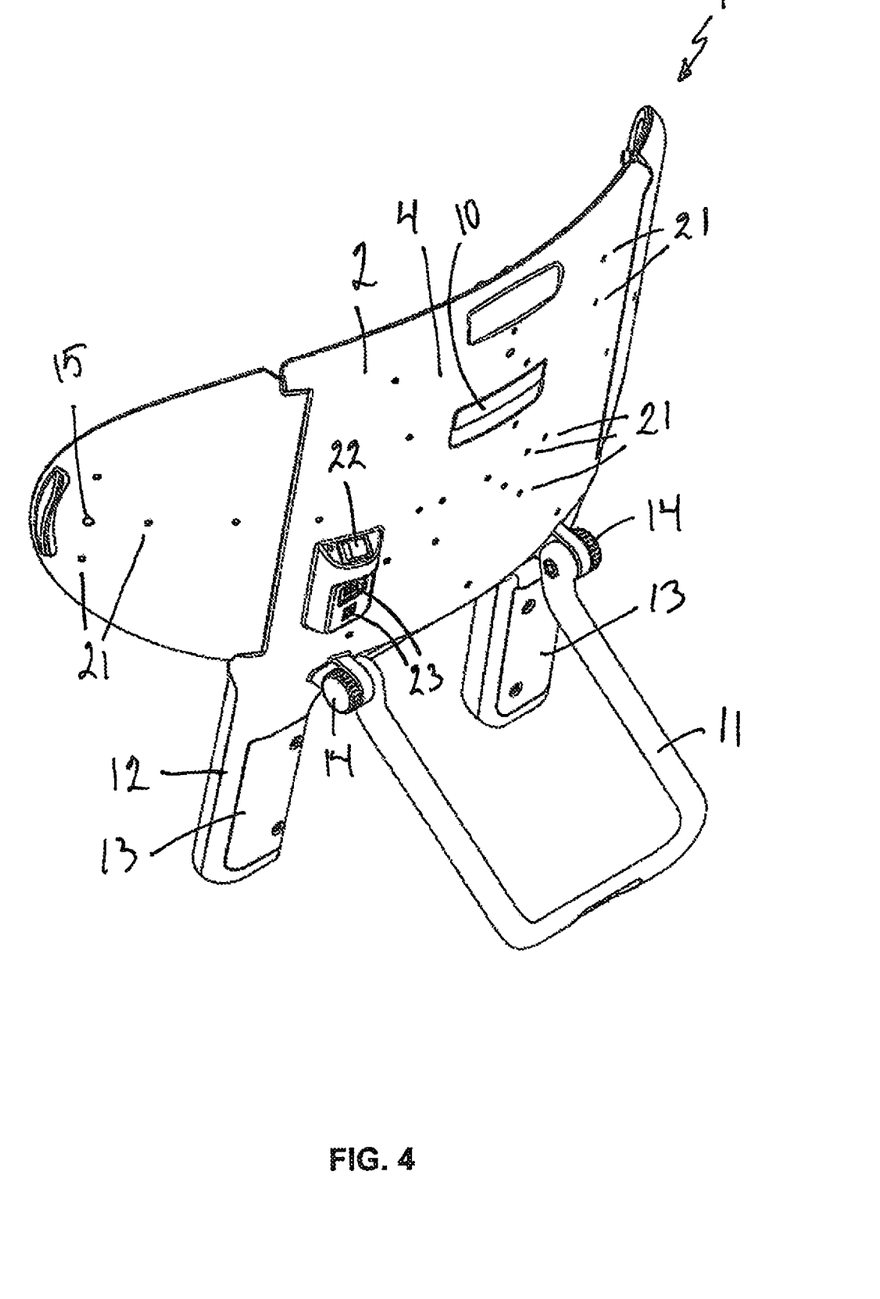
FIG. 4 shows the medical device of FIG. 3 from the second side of the perimeter surface.

The display unit 5 is arranged turnable between at least two positions, i.e. the first position (see FIG. 3) and the second position (see FIG. 1). For transport and storage, it is possible that the display unit 5 is further turned into a transport position (see FIG. 5), but this may be the same position as e.g. the first position. In the first position the display 7 can be viewed from the first side 3 of the perimeter surface, i.e. by the patient to be tested. In the second position the display 7 can be viewed from the second side 4 of the perimeter surface, e.g. by the person supervising the test. The display unit 5 may be kept in the second position e.g. when performing a test with the first testing device, i.e. with the perimeter surface 2. This way the person supervising the test may supervise and control the test with the user interface in the display unit 5.

Figure 5:
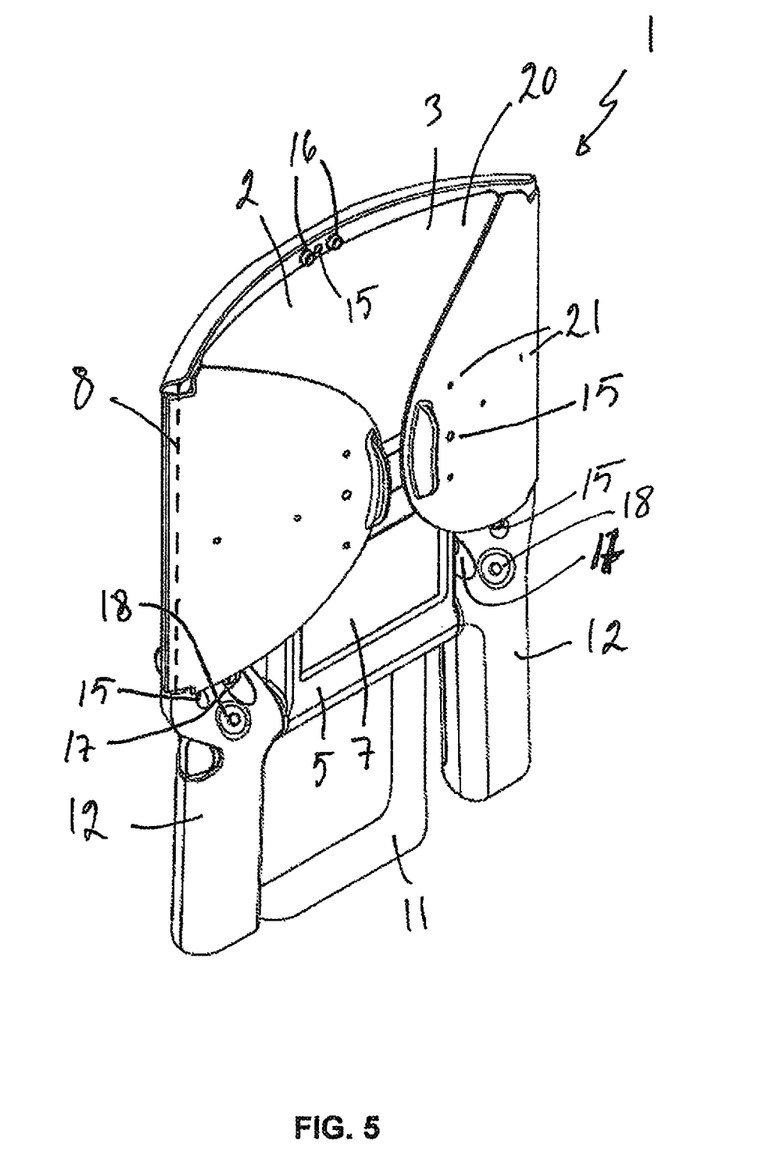
FIG. 5 shows a medical device according to the invention from the first side of the perimeter surface in a third situation.
Figure 6:
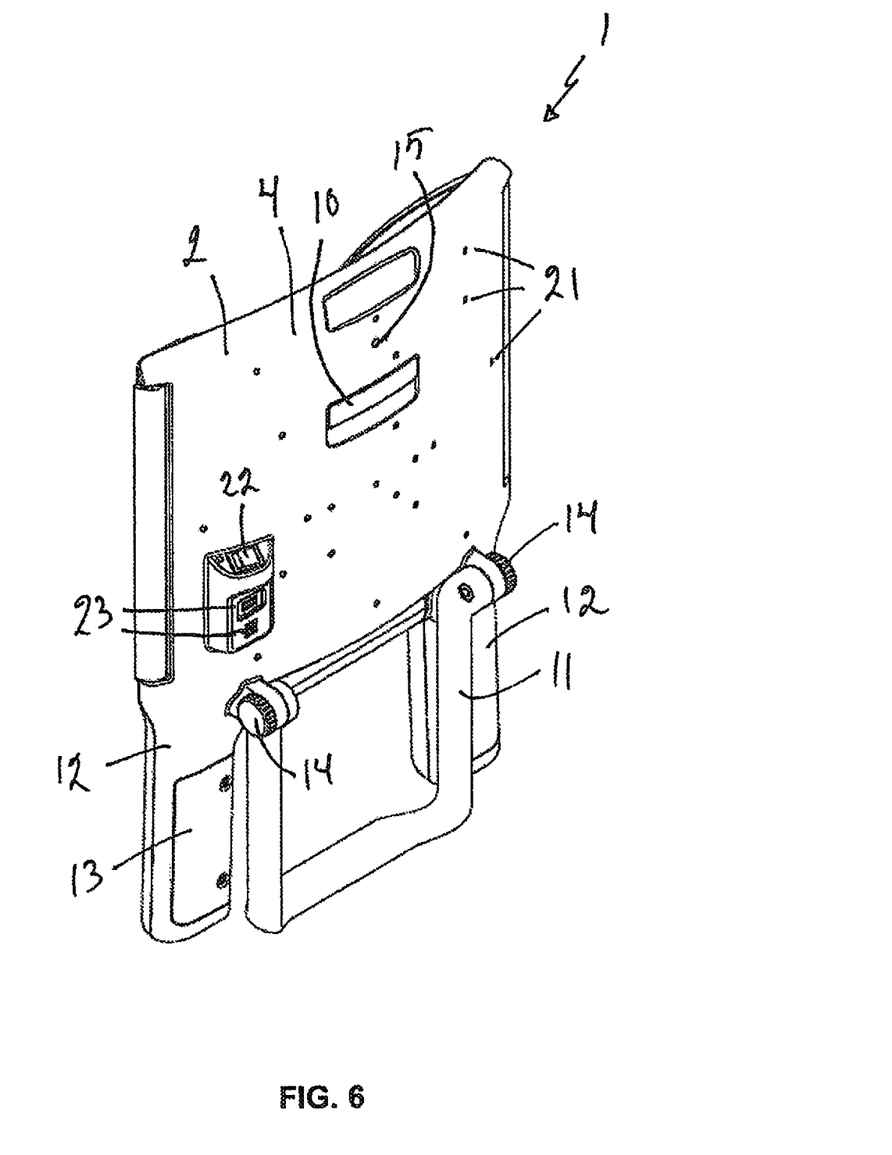
FIG. 6 shows the medical device of FIG. 5 from the second side of the perimeter surface.

The perimeter surface 2 is arranged foldable around hinges 8 between at least two positions, i.e. a use position (FIG. 1) and a transport position (FIG. 5). In the use position the perimeter surface 2 is arranged open and the first side 3 of the perimeter surface 2 may be viewed by the patient. In transport position the perimeter surface 3 is folded so that side parts 9 of the first side 3 of the perimeter surface are not viewable by the patient.

A handle 10 is situated near the top of the second side 4 of the perimeter surface 2. A turnable support leg 11 allows the device to be kept in a suitable position e.g. on a table. The support leg 11 may be turned between at least two positions, the use position (FIG. 1) and the transport position (FIG. 5). Batteries are situated in stationary legs 12, behind lids 13. The movement of the turnable support leg 11 may be controlled with clamping screws 14. Ambient light sensors 15 are arranged in the device to detect lighting conditions around the device 1 and to monitor and/or adjust the performance of the first and/or second testing devices 2, 3. Proximity sensors 16 are arranged in the device to detect the position of the patient. Glare lights 17 to be lighted towards the patient during testing of glare are situated near the display unit 5. Buttons 18 may be used by the patient in some tests, e.g. to indicate if a visual stimulus was seen.

The first testing device comprises at least one light matrix 19, such as a LED matrix or an OLED matrix or an LCD matrix, capable of displaying perimeter stimulus and/or fixation objects at least to the first side of the perimeter surface. The positions 19 of the matrix lights shown in FIG. 1 are only exemplary, the positions of the lights in the light matrix may be selected in various ways. The first side 3 of the perimeter surface 2 is covered with a translucent layer 20, which hides the light matrix 19 from the patient when the light matrix is not lighted. But when a light in the light matrix is lighted, the light is seen through the translucent layer 20.

The perimeter surface 2 comprises several small light openings 21 towards its second side 4. The openings 21 are situated at the positions where the lights, e.g. LEDs of the light matrix 19 are situated on the first side 3 of the perimeter surface 2. This way the person supervising the test from the second side 4 of the perimeter surface 2 can see where the fixation object or visual stimulus is lighted.

A power on/off-switch 22 and I/O-sockets 23 are situated on the second side 4 of the perimeter surface 2.

Figure 7A:
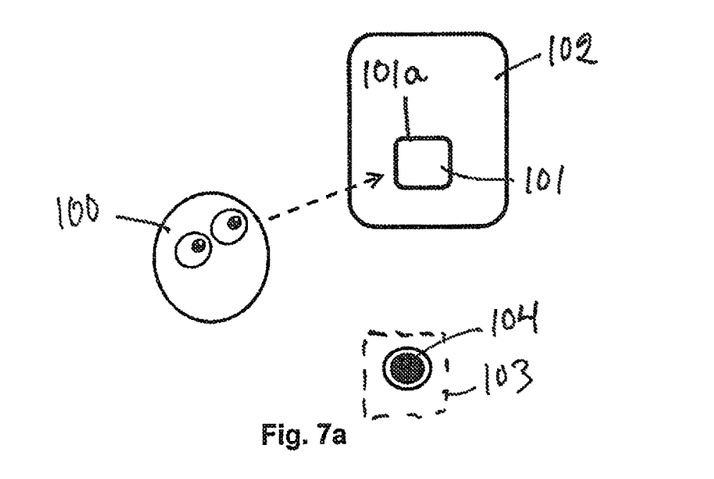
FIGS. 7*a*-7*c* show an apparatus and a method according to the invention in use.

In FIG. 7a a patient or test subject 100 is looking at a fixation point 101 with a first visual appearance 101a of a rounded rectangle. The fixation point 101 is displayed on a surface 102, such as a display screen or a perimeter surface. A response device 103, e.g. a remote control or mobile phone or a tablet computer has a button 104 to be pressed by the test subject when he/she sees a stimulus. The test subject is waiting knowing that before the stimulus is shown, the fixation point will change appearance.

Figure 7B:
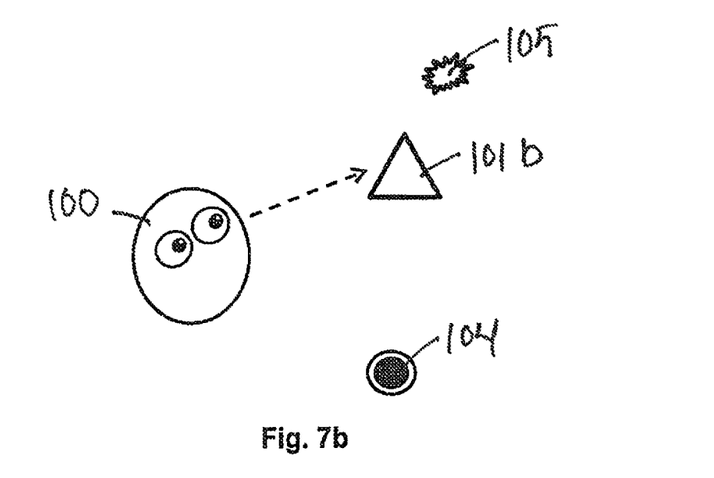

In FIG. 7b the test subject 100 is looking at the fixation point 101 and realizes it has changed to a second visual appearance 101b, a triangle. Shortly after that a stimulus 105, a flash of light is shown on the surface 102.

Figure 7C:
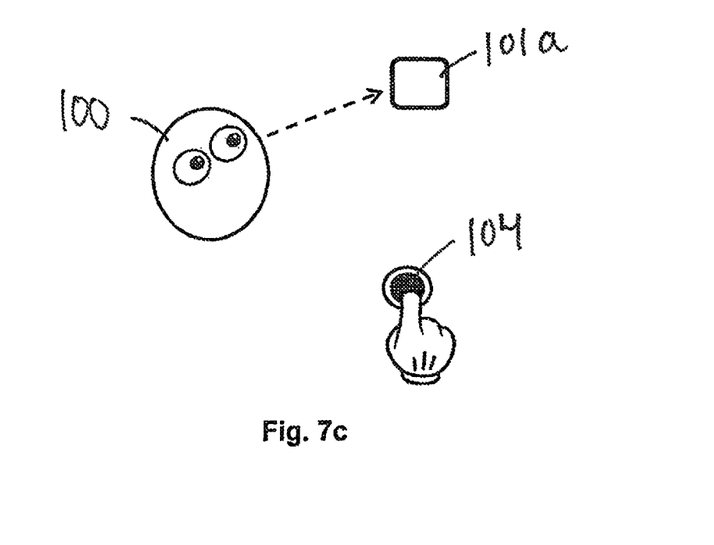

In FIG. 7c the test subject 100 responses by pushing the button 104. The fixation point 101 has changed back to its first visual appearance 101a, a rounded rectangle. Now the test subject 100 is waiting for a new test round, i.e. for the fixation point 101 to change appearance, a stimulus light flash etc.

Figure 8A:
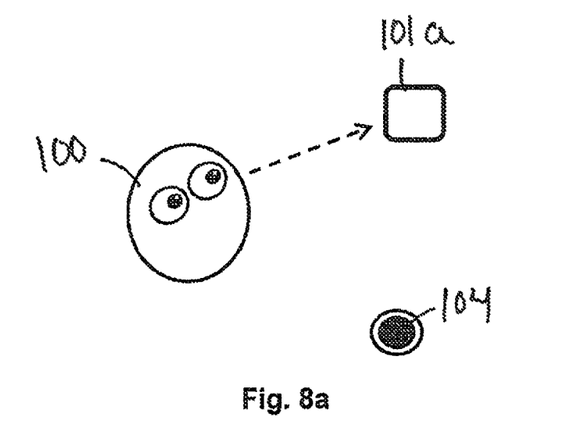
FIGS. 8*a*-8*c* show an apparatus and a method according to the invention in use.
Figure 8B:
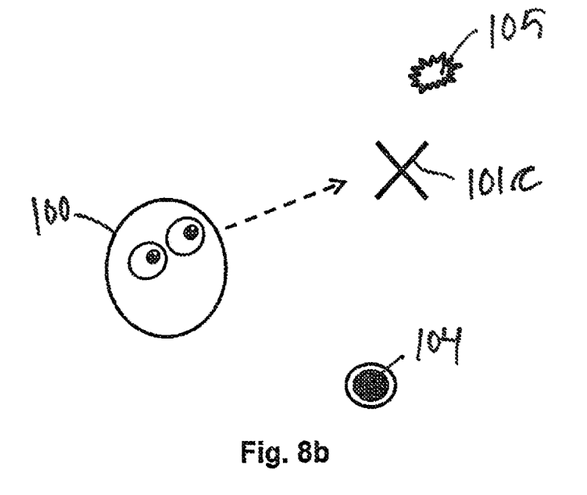
Figure 8C:
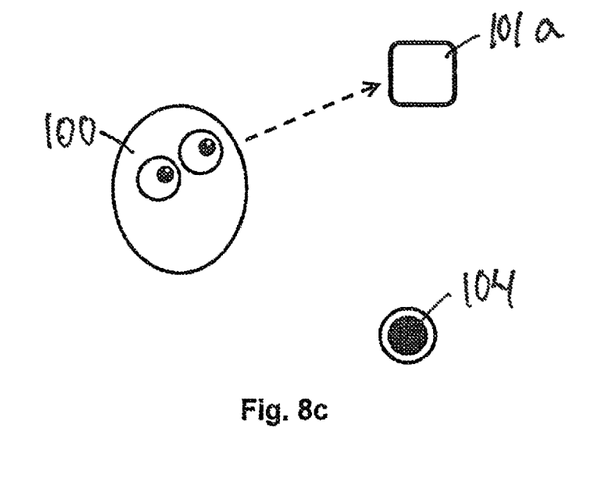

FIGS. 8a-8c show an embodiment, where the fixation point may change appearance into "do-not-response-even-if-you-see-a stimulus"-appearance. In FIG. 8a a patient or test subject 100 is looking at a fixation point 101 with a first visual appearance 101a of a rounded rectangle. The fixation point 101 is displayed on a surface 102, such as a display screen or a perimeter surface. A response device 103, e.g. a remote control or mobile phone or a tablet computer has a button 104 to be pressed by the test subject when he/she sees a stimulus. The test subject is waiting knowing that before the stimulus is shown, the fixation point will change appearance. The test subject knows that he/she is meant to press the button 104 only if the fixation point changes into a triangle 101b. If it changes into a cross 101c, the button is not to be pressed even if a stimulus is shown.

In FIG. 8b the test subject 100 is looking at the fixation point 101 and realizes it has changed to a third visual appearance 101c, a cross. This is a "do-not-response-even-if-you-see-a stimulus"-appearance. Thus, even when the stimulus 105 is shown on the surface 102, the test subject should not press the button 104.

In FIG. 8c the test subject 100 does not press the button 104. The fixation point 101 has changed back to its first visual appearance 101a, a rounded rectangle. Now the test subject 100 is waiting for a new test round, i.e. for the fixation point 101 to change appearance, a stimulus light flash etc.

The figures show only a few preferred embodiments. Facts of secondary importance with regards to the main idea of the invention, facts known as such or evident for a person skilled in the art, such as power sources or support structures possibly required by the invention, are not necessarily separately shown in the figures. It is apparent to a person skilled in the art that the invention is not limited exclusively to the examples described above, but that the invention can vary within the scope of the claims presented below. The dependent claims present some possible embodiments of the invention, and they are not to be considered to restrict the scope of protection of the invention as such.

The invention claimed is:

1. A method used in a standard automated perimetry (SAP) perimeter or campimeter with a visible fixation point, the method comprising at least the following steps:
producing a fixation point (101) having a first visual appearance (101a) to be shown to a patient (100);
producing a stimulus (105) shown to the patient at a stimulus time-point at a pre-defined location;
activating a response device (103) by the patient upon noticing the stimulus at a response time-point;
further comprising
changing the fixation point to have a second visual appearance (101b) for a fixation point second visual appearance time interval near the stimulus time-point by starting the fixation point second visual appearance time interval not earlier than 1 second before the stimulus time-point; and
changing the fixation point back to have the first visual appearance (101a) after the fixation point second visual appearance time interval has ended or after patient has responded.

2. A method according to claim 1, further comprising using ambient light sensors (15) to adjust luminance of the stimuli and fixation points during a test based on illumination of perimeter surface so that luminance contrast can be set at a desired level.

3. A method according to claim 1, wherein
starting the fixation point second visual appearance time interval less than 200 ms before the stimulus time-point, and/or
ending the fixation point second visual appearance time interval not later than 2 seconds after the stimulus time-point, or after the fixation point second visual appearance is shown, or after patient has responded.

4. A method according to claim 1, further comprising recording whether the patient activates the response device during a response time interval or not.

5. A method according to claim 1, characterized in producing a second stimulus shown to the patient at a second stimulus time-point after a stimulus time interval from either the previous stimulus time-point or the previous response time-point.

6. A method according to claim 5, characterized in varying one or more of:
the stimulus time interval
light intensity of the stimulus
stimulus size
stimulus color
stimulus location.

7. A method according to claim 5, characterized in varying the position of the fixation point shown to the patient.

8. A method according to claim 1, characterized in changing the fixation point to have a third visual appearance for a time interval near the stimulus time-point when the patient should not activate the response device even if he/she saw the stimulus.

9. A standard automated perimetry (SAP) perimeter or campimeter with a visible fixation point comprising
means for producing a fixation point (101) having a first visual appearance (101a) to be shown to a patient (100);
means for producing a stimulus (105) shown to the patient at a stimulus time-point;
a response device (103) adapted to be activated by the patient upon noticing the stimulus at a response time-point;
characterized in that the means for producing a fixation point are arranged to
change the fixation point to have a second visual appearance (101b) for a fixation point second visual appearance time interval near the stimulus time-point, starting the fixation point second visual appearance time interval not earlier than 1 second before the stimulus time-point;

change the fixation point back to have the first visual appearance (101*a*) after the fixation point second visual appearance time interval has ended or after patient has responded.

10. A perimetry or a campimeter according to claim 9, further comprising ambient light sensors (15) adapted to adjust luminance of the stimuli and fixation points during a test based on illumination of perimeter surface so that luminance contrast can be set at a desired level.

11. A stand-alone medical device (1) for testing a patient, which comprises in one-piece configuration:

a first testing device comprising a perimeter surface (2) having a first side (3) to be viewed by the patient during testing and second side (4) not to be seen by the patient during testing, one or more second testing devices (5, 7) from the group of:
  a) a visual acuity measurement device to be viewed by the patient during testing of visual acuity,
  b) a contrast sensitivity testing device to be viewed by the patient during testing of contrast sensitivity,
  c) a glare testing device to be viewed by the patient during testing of glare, user interface device (7, 18) for controlling the use of the first and second testing devices, a perimeter or a campimeter according to claim 9.

* * * * *